US006886061B2

(12) United States Patent
Yokota et al.

(10) Patent No.: US 6,886,061 B2
(45) Date of Patent: Apr. 26, 2005

(54) ELECTRONIC RECORD SYSTEM AND CONTROL PROGRAM DEVICE WITH DISPLAY AND TABLET FUNCTION FOR MANIPULATING DISPLAY AREA FUNCTIONS WITH PEN STYLUS

(75) Inventors: Hiroshi Yokota, Osaka (JP); Takeo Igarashi, 2-5-11, Matsugaoka, Chigasaki-shi, Kanagawa (JP); Kazuo Nakazawa, 3-50-D10-104, Aoyamadai, Suita-shi, Osaka (JP); Takashi Ashihara, Otsu (JP); Takenori Yao, Kusatsu (JP); Hiroyuki Sakachi, Osaka (JP)

(73) Assignees: NEC Corporation, Tokyo (JP); Takeo Igarashi, Kanagawa (JP); Kazuo Nakazawa, Osaka (JP)

( * ) Notice: Subject to any disclaimer, the term of this patent is extended or adjusted under 35 U.S.C. 154(b) by 55 days.

(21) Appl. No.: 10/300,890

(22) Filed: Nov. 21, 2002

(65) Prior Publication Data

US 2004/0003142 A1 Jan. 1, 2004

(30) Foreign Application Priority Data

Nov. 22, 2001 (JP) ........................................ 2001-357736

(51) Int. Cl.[7] .............................. G06F 3/00; G06F 13/00
(52) U.S. Cl. ................................ 710/73; 710/1; 710/14; 710/72; 710/74; 705/1; 705/2; 705/3; 705/4; 705/5; 600/523
(58) Field of Search .......................... 710/1, 14, 72–74; 702/1–5; 600/523

(56) References Cited

U.S. PATENT DOCUMENTS

| 5,561,446 | A | * | 10/1996 | Montlick ..................... 345/173 |
| 5,724,985 | A | * | 3/1998 | Snell et al. .................. 600/523 |
| 5,867,821 | A | * | 2/1999 | Ballantyne et al. ............ 705/2 |
| 6,314,405 | B1 | * | 11/2001 | Richardson ..................... 705/3 |
| 6,393,404 | B1 | * | 5/2002 | Waters et al. ................... 705/2 |
| 6,421,650 | B1 | * | 7/2002 | Goetz et al. ................... 705/3 |
| 6,711,547 | B1 | * | 3/2004 | Glover .......................... 705/2 |
| 2002/0032584 | A1 | * | 3/2002 | Doctor et al. .................. 705/3 |
| 2002/0091659 | A1 | * | 7/2002 | Beaulieu et al. ............. 706/62 |

FOREIGN PATENT DOCUMENTS

JP      2000-325314 A    11/2000

* cited by examiner

*Primary Examiner*—Tammara Peyton
(74) *Attorney, Agent, or Firm*—Sughrue Mion, PLLC

(57) ABSTRACT

Disclosed is an electronic record system which dispenses with complicated operations using a menu and a button and handwriting input operation like paper writing can be achieved. A system is established and is provided with: an input/output unit device capable of inputting/outputting data by the direct writing on a display screen with a pen; and a control/arithmetic device connected to the input/output unit device and reflecting the data inputted on the display screen to the screen. In this system, an electronic record in the form of strip-shaped sheet with an infinite length extending in the longitudinal direction is displayed, data is directly inputted from the display screen as a stroke data, the inputted characters are converted into the character data by the use of a character recognition engine and the converted data is used as data format available in a secondary use such as a data search, and various functions are driven by a predetermined pen operation.

41 Claims, 12 Drawing Sheets

ELECTRONIC RECORD SYSTEM AND CONTROL PROGRAM DEVICE WITH DISPLAY AND TABLET FUNCTION FOR MANIPULATING DISPLAY AREA FUNCTIONS WITH PEN STYLUS

BACKGROUND OF THE INVENTION

1. Field of the Invention

The present invention relates to an electronic record system provided with a pen type input device and an output device for displaying an electronic record. More specifically, the present invention relates to an electronic medical record system and a control program thereof wherein an input/output operation is improved. Although the following description will be mainly directed to an electronic medical record system, it is to be noted throughout the instant specification that the present invention is applicable to any other electric record system than the electronic medical record system.

2. Description of the Related Art (1) Technical Background

Heretofore, in medical care sites, a medical record has been made up by writing a medical condition and progress of a patient in accordance with a time sequence.

For the medical record, a piece of paper is used as a recording medium, and hence, needless to say, "handwriting" is essential for making up the medical record. In this connection, such a conventional system may be referred to as a paper medical record system. If necessary, a figure or a graph, such as a standard figure of the heart or the lung is often pasted in relation to medical care. In addition, a printed matter that prints medical data may often be pasted on the medical record. Tugs may be applied or attached to written pieces of paper to be stored in individually colored files. This facilitates visual-based management. Furthermore, such medical records can be quickly seen or checked and therefore have a superior flexibility.

However, the paper medical record system has some problems. Specifically, a great amount of paper makes it difficult to ensure a storage space for the medical records.

Herein, it is to be noted that Medical Practitioners Law in Japan requires keeping the medical records for five years. However, five-years preservation of the medical records is not always long enough to ensure complete recovery in some cases. Therefore, such medical records should preferably not be discarded even after the five-years preservation. Further, even if some medical information should be modified from an original medical record, a modified record must be compulsorily left together with the original record prior to the modification, in order to avoid falsification the record before the modification. As a result, the amount of information to be preserved is apt to be increased.

As described above, in addition to the preservation duty of the medical records, there are "bulky" medical records concerned with patients who are hospitalized for long periods and/or who are subjected to long-term curing as regular outpatients. This results in inevitable lack of the storage space and further requires ensuring new storage space. Moreover, such a system increases a cost and further makes it difficult to find out a desired medical record.

Under the circumstances, with the recent development of the computerization technology, proposals have been made about various electronic medical record systems in which the contents of medical care can be stored. With this system, reference and modification of the medical records can be performed at any time.

This system is obtained by computerizing the conventional "paper" medical record system and has been started from the announcement of the Ministry of Health and Welfare in Japan. The announcement was issued to medical institutions across the country through prefectural and city governments in September 1999 and admitted electronic records as official medical records. Thereafter, the electronic medical record system has rapidly widespread in medical care sites at present.

Adopting the electronic records as described above makes it possible to unitarily preserve and manage the electronic records and to share them. Also, it is possible to perform keyword search from a great amount of data. Although the paper medical record system requires enormous cost and space for preserving information (paper medical record and the like) concerning medical care, the electronic medical record system can solve such problems. This is one of the favorable features of the electronic medical record system.

On the other hand, some novel problems take place in a conventional electronic medical record system. Specifically, the conventional electronic medical record system is constituted of a control/arithmetic device, an input device including a key board and a mouse, and an output device including a display device and a printer device. This system is disadvantageous in that the input operation of medical information is so difficult and, as a result, imposes a heavy load on a doctor so as to effectively operate the key board and the mouse.

Consequently, each doctor should devote himself/herself to the input operation in such a conventional electronic medical record system and may interrupt his/her thought about the medical care due to such an input operation. Also, seeing a doctor who desperately operates an input device, such as the key board, the mouse, makes a patient anxious about whether the patient has oneself carefully examined by the doctor.

In order to reduce a load imposed on each doctor at the time of inputting the medical information, consideration has been made about a "pen tablet" method. According to this method, an input operation can be performed in a manner similar to that performed on a paper media as an input device.

(2) Prior Art

As an example of the system using this pen tablet, disclosure is made in Japanese Unexamined Patent Publication No. 2000-325314 about an electronic record storage device and a method thereof.

This device essentially provides a medical record image or screen for displaying predetermined contents in a limited region. In this device, data input operation is performed by the use of a liquid crystal pen tablet by successively selecting a menu and buttons.

Specifically, an operator can input data by sequentially selecting items from the menu and buttons on the medical record image or screen when the items specify desired contents, looking at the medical record screen displayed on the output device. When comments or the like can not be entered by selecting items, they are inputted by using a key board. Such comments may be inputted by using the method disclosed in the Japanese Unexamined Patent Publication No. 2000-325314 (disclosed in FIG. 26). In this event, characters can be written in a predetermined frame or window with a pen and are converted into character data by a character recognition technique.

However, the above-mentioned system has the following problems.

The first problem is that the device essentially selects the menu and button and, therefore, each operator must comprehend a complicated specification of the menu and buttons, and thus, hospitals may be likely to hesitate to introduce the device.

The second problem is that, although the pen tablet is used in the system, an easy input operation like handwriting can not be accomplished because final input operation needs to manipulate the arranged menu and buttons. As a result, a very long time is wasted to be accustomed to manipulation.

The third problem is that, since most of the operations are performed by selecting the menu and buttons arranged on the screen, it is impossible to rapidly input what comes to mind. As a result, such an input operation may cause a doctor to lose his/her train of thought and erroneous diagnosis may be made by the doctor.

The fourth problem is that, since only predetermined items can be entered while any other items can not be inputted, restrictions are imposed on items to be entered.

The fifth problem is that, since a screen must be switched to another screen to make access to past data. It is impossible to display the past medical record simultaneously with the current medical record to which data is being inputted. No input operation can be performed, with the past medical record being displayed.

The sixth problem is that, since characters must be written in the predetermined frame or window in the case of the character recognition, it is impossible to perform the character recognition of handwritten characters written in an optional space or place.

The seventh problem is that, since the character recognition requires writing characters on a character input sheet, such handwritten characters themselves can not be confirmed later.

SUMMARY OF THE INVENTION

The present invention has been developed to solve these problems.

It is an object of the present invention to provide a user-friendly electronic record system and a control program thereof in which a pen type input device is used to enable free-writing input operation and to alleviate stress due to a complicated input operation.

It is a specific object of the present invention to provide an electronic record system of the type described, which is effectively used as an electronic medical record system.

It is another specific object of the present invention to provide a control program of the type described, which is available for the electronic medical record system.

In order to solve the above-described problems, an electronic record system and a control program thereof according to the present invention are featured by the following matters.

An electronic record system of the present invention comprises an input/output unit device which has a display device with a tablet function and which executes input operation by directly writing input data on the display device with a pen, and a control/arithmetic device, connected to the input/output unit device, for reflecting on the display device the input data entered on the display device. The control/arithmetic device is adapted so as to display, on the display device, a record screen in which the input data is intuitively written by direct handwriting and so as to establish an electronic record on the basis of the data inputted on the medical record screen by the handwriting.

The electronic record is computerized like a stripe-shaped sheet with an infinite length extending in a vertical direction of the display screen, and the control/arithmetic device is configured so that the electronic record displayed on the display device can be scrolled.

The record screen comprises a reduced-size display area on which past information on a past date specified by date information is longitudinally displayed in a reduced size, and an actual-size display area on which detailed information is handwritten and current information is longitudinally displayed in an actual size.

The record screen preferably further includes a date display area for displaying a succession of dates longitudinally.

The control/arithmetic device is preferably configured so that the date display area, the size-reduced display area and the actual-size display area can be independently longitudinally scrolled.

The control/arithmetic device is preferably configured so that the date display area and the reduce size display area are scrolled together by vertical drawing on these areas. Desired past information is duplicated onto the actual-size display area by drawing so as to surround a desired region of the past information displayed on the reduced-size display area with a substantial circle, and by drawing from the inside of the drawn substantial circle to the outside.

The input data is constituted of written information and data processing information, and the input/output unit device is configured so as to select writing operation and data processing operation in accordance with an input mode of the pen.

The written information is preferably composed of a written record and partition line information that is entered by linear drawing in the horizontal direction of the display screen, so as to end the writing operation. The control/arithmetic device comprises first determination means for determining whether the written information is either the written record or the partition line information. When it is determined that the written information is the partition line information, a drawn line is not treated as stroke data and a partition line is displayed on the record display screen to store the written information.

The first determination means determines whether the written information is the written record or the partition line information, with reference to a relationship between an entire length of the drawing and a straight distance from a starting point to an end point of the drawing, a relationship between a width of a line segment formed by the drawing and a width of the record screen, and a straight distance in the vertical direction of the line segment formed by the drawing.

The data processing information is composed of area selection information inputted by drawing so as to surround a desired area with a circle and pie menu process information inputted by linear drawing for executing processes registered in advance. The control/arithmetic device comprising second determination means for determining whether the inputted data is the area selection information or the pie menu process information. When the second determination means determines the inputted data as the area selection information, image processing to the selected desired area is performed, and when the second determination means determines the inputted data as the pie menu process information, a data input support process or an application starting process is performed.

The image processing operation includes enlargement, reduction, rotation, movement, duplication, deletion, and character data conversion.

The control/arithmetic device is configured so that image processing operations are selected in accordance with a direction of the drawing performed across the selected area or the drawing performed in an optional direction from the drawn line.

The data input support process is for processing undo, redo and schema. The control/arithmetic device is configured so that when the schema is selected, a schema image list is displayed and a desired schema image is duplicated on the electronic record by the use of the pen.

The application includes a computing function using handwriting character recognition and a three-dimensional figure forming function for converting the two-dimensional handwritten input or the schema image into a three-dimensional image.

The control/arithmetic device is configured so that the pie menu processes are selected in accordance with a direction of the drawing optionally performed so as not to cross the selected area.

The control/arithmetic device is configured so that when the second determination means determines that the inputted data is the area selection information, an area surrounded with a substantial circle is colored with a translucent color to indicate that the area is selected.

The application is adapted to be operated by the use of a translucent window formed on the electronic record, and the application is adapted to be finished by a pen input on the outside of the window.

The control/arithmetic device is configured so that a request section is displayed on the record screen, while a list constituted of index sections and name sections assigned in each index section are displayed by the pen operation on the request section, and a desired name is displayed in the request section by operating the pen on the desired name.

The control/arithmetic device is configured so that an order of items displayed in the name section is sorted in accordance with a frequency of selection of the items, and the list is dynamically modified by increasing/decreasing the number of the names displayed in the name section.

When the pen operation on the index section in the list is performed, all names linked with the index are displayed, and a desired name is displayed on the request section and registered in the name section by the pen operation on the desired name.

A control program to which the present invention is applicable is for use in an electronic record system comprising an input/output unit device which has a display device with a tablet function and which executes input operation by directly writing input data on the display device with a pen, and a control/arithmetic device, connected to the input/output unit device, for reflecting on the display device the input data entered on the display device. According to the present invention, the control program comprises the steps of displaying on the display device a record screen in which the input data is intuitively written by direct handwriting and establishing an electronic record on the basis of the handwritten input information on the record screen displayed by the display step.

The electronic record is computerized so as to be a stripe-shaped sheet with an infinite length extending in a vertical direction of the display screen, and the control/arithmetic device is configured so that the electronic record displayed on the display device is scrolled.

The record screen comprises a reduced-size display area on which past information in a past date specified by date information is longitudinally displayed in a reduced size, and an actual-size display area on which detailed information is handwritten and current information is longitudinally displayed in an actual size.

The record screen further comprises a date display area in which a succession of dates are longitudinally displayed.

The control program is constituted so that the date display area, the size-reduced display area and the actual-size display area are independently longitudinally scrolled.

The date display area and the reduce-size display area are scrolled together by vertical drawing on these areas, and desired past information is duplicated on the actual-size display area by performing the drawing so as to surround a desired region of the past information displayed on the reduced-size display area with a substantial circle and the drawing from the inside of the circle to the outside.

The inputted data is constituted of written information and data processing information. The control program further comprises the step of selecting writing operation and data processing operation in accordance with an input mode of the pen.

The written information is constituted of a written record and partition line information that is inputted by linear drawing in the horizontal direction of the display screen, so as to finish the writing operation. The control program further comprising the steps of determining whether the written information is the written record or the partition line information and treating a drawn line as no stroke data when it is determined that the written information is the partition line information, to display a partition line on the record display screen to store the written information.

The determination step determines whether the written information is either the written record or the partition line information, on the basis of a relationship between an entire length of the drawing and the straight distance between a starting point and an end point of the drawing, a relationship between a width of a line segment formed by the drawing and a width of the medical record screen, and a straight distance in the vertical direction of the line segment formed by the drawing.

The data processing information is constituted of area selection information inputted by drawing so as to surround a desired area with a circle, pie menu process information inputted by linear drawing for executing processes registered in advance. The control program further comprising the steps of judging whether the inputted data is the area selection information or the pie menu process information, carrying out image processing to the selected area when the judging step judges the area selection information, and carrying out a data input support process or an application starting process when the judging step judges the pie menu process information.

The image processing includes enlargement, reduction, rotation, movement, duplication, deletion, and character data conversion.

The control program is constituted so that the image processing operations are selected in accordance with a direction of the drawing performed across the selected area or the drawing performed in an optional direction from the drawn line.

The data input support process is for processing undo, redo and schema. The control program is configured so that when the schema is selected, a schema image list is displayed and a desired schema image can be duplicated on the electronic record by the pen operation.

The application includes a computing function using handwriting character recognition and a three-dimensional figure forming function for converting the two-dimensional handwritten input or the schema image into a three-dimensional image, and the respective functions work in cooperation with each other.

The control program is constituted so that the pie menu processes are selected in accordance with a direction of the drawing optionally performed so as not to cross the selected area.

The control program is constituted so that an area surrounded with a substantial circle is colored with a translucent color to indicate that the area is selected, when the judging step judges that the inputted data is the area selection information.

The application is adapted to be operated by the use of a translucent window formed on the electronic record, and the application is adapted to be finished by a pen input on the outside of the window.

The control program is constituted so that a request section is displayed on the record screen while a list constituted of index sections and name sections assigned in each index section are displayed by the pen operation on the request section, and a desired name is displayed in the request section by the pen operation on the desired name.

In the control program, an order of items displayed in the name section is preferably sorted in accordance with a frequency of selection of items, and the list is dynamically modified by increasing/decreasing the number of names displayed in the name section.

In this event, when the pen operation on the index section in the list is performed, all names linked with the index are displayed, and a desired name is displayed on the request section and registered in the name section by the pen operation on the desired name.

In the above, the electronic record may be, for example, an electronic medical record. In this case, the items and the list may be medicines and a medicine list, respectively.

DESCRIPTION OF THE PREFERRED EMBODIMENTS

Now, embodiments of an electronic medical record system according to the present invention will be described based on the accompanying drawings. FIGS. 1 to 12 exemplify the first embodiment, FIGS. 13 and 14 exemplify the second embodiment, and FIGS. 15 and 16 exemplify the third embodiment, respectively.

First Embodiment

Figure 1:
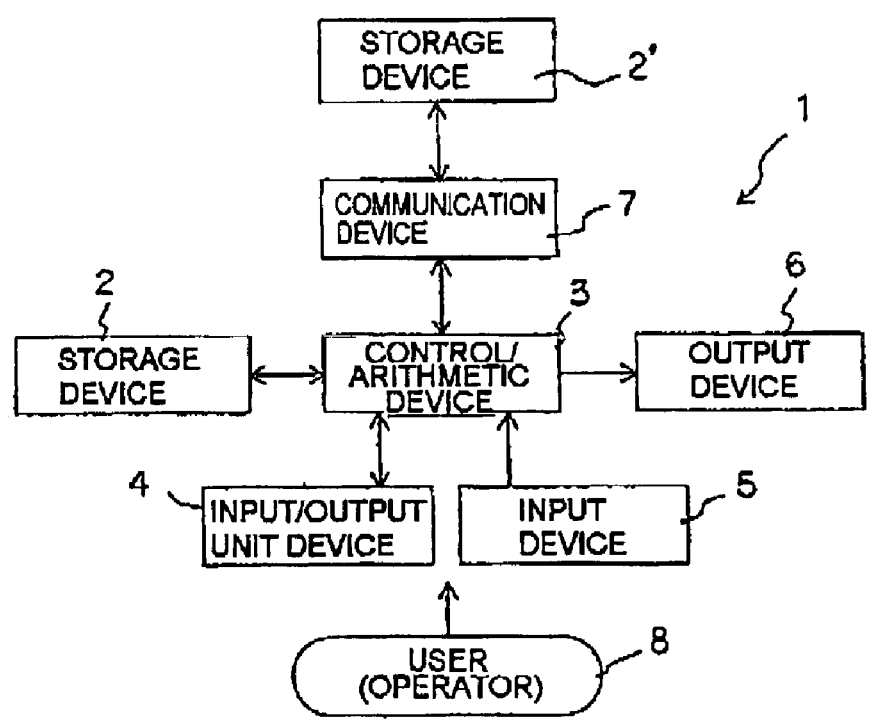
FIG. 1 is a block diagram of an electronic medical record system according to the first embodiment of the present invention.

Referring to FIG. 1, an electronic medical record system 1 according to the first embodiment of the present invention basically has an input/output unit device 4, a control/arithmetic device 3 having a two-way communication with and connected to the input/output unit device 4, and a storage device 2 having a two-way communication with and connected to the control/arithmetic device 3. In addition, the system has an output device 6 such as a printer, an input device 5 such as a mouse and a keyboard, and a storage device 2' connected to a network via a communication device 7 through a network. The output device 6, the input device 5 and the storage device 2' connected through the network are not essential for the present invention and, therefore, will not be described in detail.

Herein, it is to be noted that the input device 5, such as a mouse or a keyboard, is shown in FIG. 1 and is used only to input an identification number or the like assigned to each patient. Therefore, the input device 5 may not be practically used while diagnosis is being actually made by a doctor.

The input/output unit device 4 is implemented by a display device with a pointing device, that has a tablet function. Such a display device is well-known in the art and can enter data by directly writing on a display screen with a pen.

The storage device 2 includes a hard disk which stores a predetermined control program for executing functions of the first embodiment together with the electronic records in the past. In addition, the storage device 2 further includes a memory device used to operate the system, and a removable media device which is readable and writable and which may be, for example, a magnetic disk and/or an optical disk, such as CD-R, CD-RW, and DVD-R. The control/arithmetic device 3 is connected to the input/output unit device 4 and the storage device 2 and can carry out two-way communication with the devices 4 and 2 in accordance with a predetermined control program. The control/arithmetic device 3 is operated to reflect input information or data inputted by a pen onto the display device.

Brief description will be made below about operations of the electronic medical record system 1 according to the first embodiment and composed as described above. First, data is fetched from the storage device 2, to form a medical record screen. Then, the medical record screen is displayed on the input/output unit device 4 or printed out from the output device 6. A doctor enters data through the input/output unit device 4, looking at the screen. The control/arithmetic device 3 updates the medical record screen based on the inputted data, and the updated data is displayed on the input/output unit device 4. When the doctor selects an end of the operation, the control/arithmetic device 3 stores the formed medical information in the storage device 2 as an electronic record. Hereinafter, more detailed descriptions will be made hereinafter.

Figure 2:
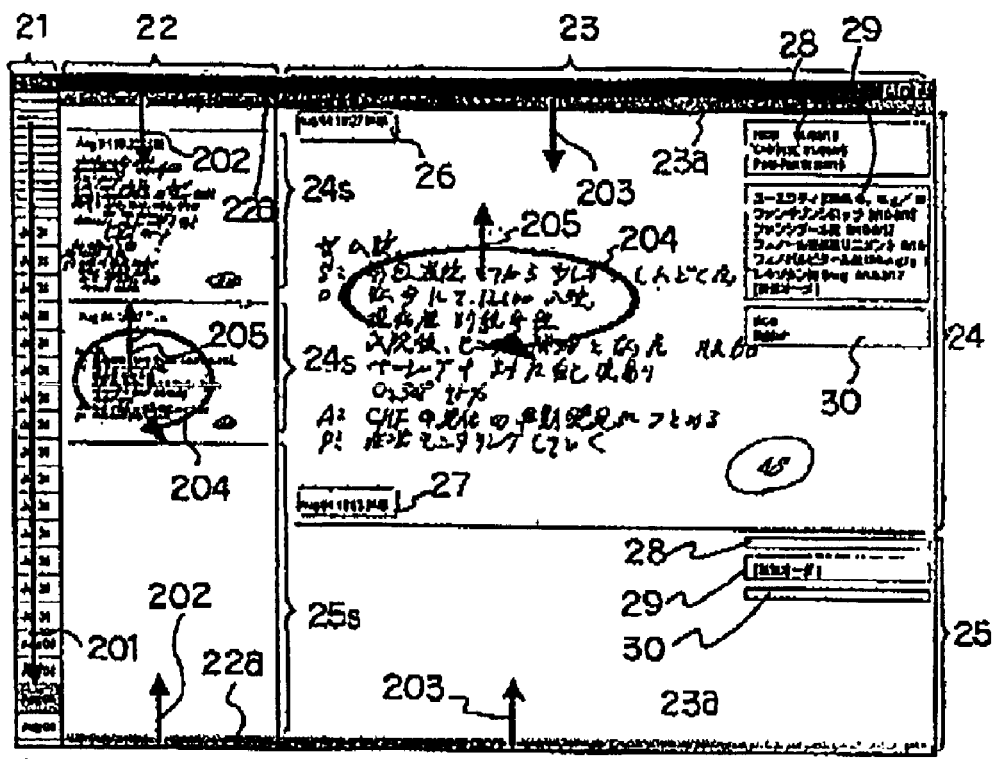
FIG. 2 is an explanatory diagram showing the configuration of the medical record screen according to the first embodiment.

A medical record image or screen (or a display image) of the electronic medical record system according to the first embodiment is exemplified in FIG. 2. The medical record image shown in FIG. 2 is composed of a date display area 21, a size-reduced display area 22, and an actual-size display area 23. Consequently, the image or screen is divided into three zones to display information in three divided stages.

The date display area 21 is placed on the left end of the display image and is extended from top to bottom to display a succession of dates. Dates in the date display area 21 are automatically displayed in cooperation with a timer of the system when the electronic record is made up.

The size-reduced display area 22 is for displaying a scroll bar 22a, a size-reduced past data sheet 24s in which previous medical information is entered on a previous date displayed on the date display area 21 and is displayed in a reduced size, and a size-reduced current data sheet 25s. The size-reduced display area 22 is placed adjacent to the date display area 21.

The actual-size display area 23 is adjacent to the size-reduced display area 22. The illustrated actual-size display area 23 has a scroll bar 23a, a past data sheet 24 displayed in an actual size and extended in a direction from top to bottom, and a current data sheet 25 extended in a direction from top to bottom and displayed in an actual size. In addition, the actual-size display area 23 also includes a sheet forming date section 26, a sheet formation end date section 27, a medical history section 28, and treatment sections 29 and 30. In the illustrated example, the treatment sections are individually used as a medical prescription request section 29 and a medical check request section 30.

The detailed medical information is directly written with a pen by the doctor in the actual-size display area 23, and a medical record is entered and modified in this area 23.

Now, description will be directed to a pens that is used in this embodiment and that has a tablet function. It is assumed that the pen is operated in two different data input modes, for example, a data input (writing) mode and a data processing (control) mode. In addition, either of the writing mode or the data processing mode can be selected by manipulating the pen, for example, pushing a button attached to the pen.

The writing mode is simply to perform drawing on the actual-size display area like writing on a paper. However, depending on the motion of the drawing and the place where the drawing is performed, the drawing is considered to be the writing of the medical record or partition line information (a ruled line is drawn) which controls the system to perform the scroll (a displayed region is moved in a longitudinal direction) or the end of the writing of the medical record.

The partition line information may be entered to finish or end the writing of the medical record. To this end, the operation thereof can be accomplished by simply drawing a straight line in the width direction of the medical record screen. The drawn straight line is not practically shown on the screen and only the partition line (ruled line) appears on the screen. By drawing the partition line, the operation of writing the medical record is finished once. In any other writing operations than drawing the partition line, characters and figures are judged to be written and entered as stroke data. In this event, the drawn characters and figures are displayed on the screen.

In this case, a problem arises. That is, it is difficult for the system to determine whether characters and figures are written simply or the partition line is written. The way to deal with the problem will be described later.

The data processing mode is to perform the drawing, for example, by pushing a button provided on the pen. Depending on the shape and order of the drawing, the drawing is branched into a process for area selection information and a pie menu process, in a manner to be described later.

In the case of the area selection, a desired area is surrounded by a circle and the surrounded area is colored in a translucent color. This shows that the area is selected. It is possible to perform processes of enlargement, reduction, rotation, and movement of stroke data in the selected area, image processing such as deletion thereof, and conversion of the stroke data into character data by the use of a character recognition engine provided in the system. The conversion into the character data makes it possible to perform a keyword search from a great amount of accumulated medical data (character data).

In these processes after the area selection, drawing for information processing is made so that a line segment crosses the selected area or is derived from a drawn line segment in an optional direction. In this case, various different image processing is selected in accordance with the direction drawn.

It is to be noted that, in the case where the drawing in the data processing (control) mode is performed to roughly draw a circle, a complete circle may not always be drawn and, therefore, a starting point may not be connected to a finish or an end point. From this fact, it is readily understood that an incomplete circle is automatically complemented when the drawing is judged to be the area selection.

In the pie menu processing, drawing for the data processing mode is made linearly in an optional direction without any area selection. Thus, various pie menu processes registered in advance are selected and executed in accordance with the direction of the drawing.

The pie menu is constituted of input support operations, such as undo (retry), redo (retry again), and schema (an image of an affected portion) selection and various applications registered in advance.

The date display area 21, the size-reduced display area 22, and the actual-size display area 23 are computerized and displayed so that an endless strip-shaped sheet with an infinite length is like extending in the longitudinal direction of the display device from top to bottom. When vertical drawing is made along the date display area 21 in the writing (input) mode, both the date display area 21 and the reduced-size display area 22 are scrolled together. For example, when a drawing operation 201 is performed, as shown in FIG. 2, the past data sheets 24s are successively displayed on the size-reduced display area 22 from top to bottom.

In addition, a scroll of the size-reduced display area 22 in the longitudinal direction by a drawing operation 202 in the writing (input) mode can be separately performed from a scroll of the actual-size display area 23 in the longitudinal direction by a drawing operation 203.

Drawing with the data processing (control) mode is performed to surround a desired area of the past medical information (sheet) displayed on the size-reduced display area 22 with a circle, and then, the drawing from the drawn circle to the outside is performed, thereby the area in the circle is quickly displayed on the actual-size display area 23. By such an operation, it becomes possible to rapidly browse a great amount of the past data sheet, and easy searching of the required data can be performed.

As described above, the doctor can perform the input work while checking past medical record of a patient, and also, he/she can easily duplicate important information into the actual-size display area 23 then used.

Addition and modification of data can be made only on the current data sheet 25 of the actual-size display area 23. In other words, past medical information cannot be modified. However, as described above, it is possible to effectively use the past data by duplicating or copying the data to the current data sheet 25. The duplication of the past data is performed in the following manner. That is, a drawing 204 in the data processing mode is made on the past data sheet 24 or the size-reduced past data sheet 24s to select an area. Then, an operation depicted by 205 is executed to draw a line from the inside of the selected area to the outside. Thus, the past data in the selected area is duplicated or copied on the current data sheet 25.

Figure 3:
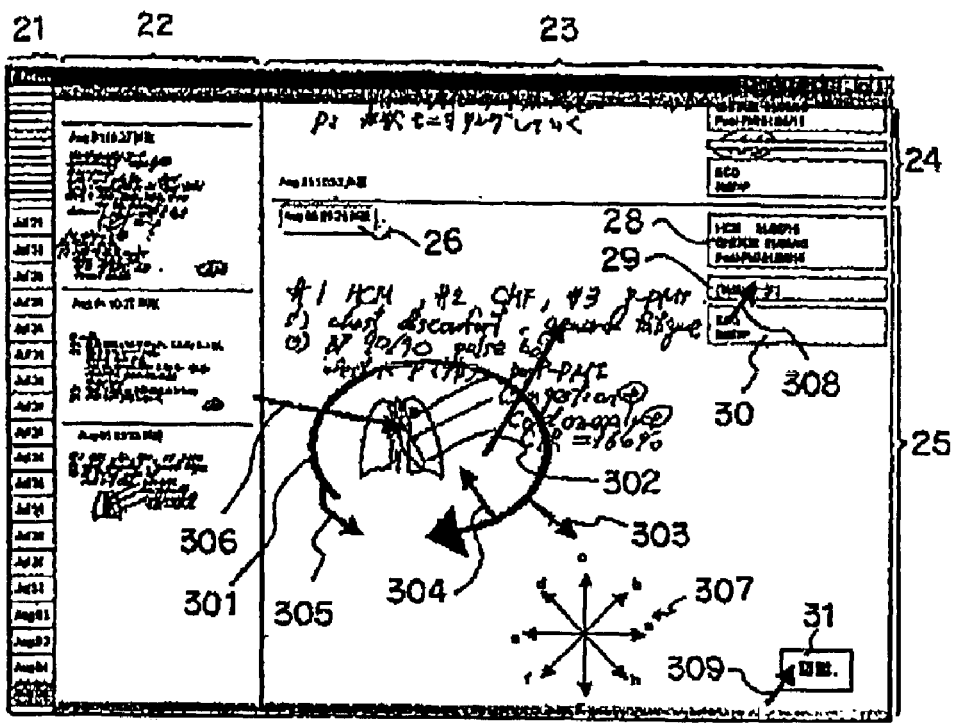
FIG. 3 is an explanatory diagram continued from FIG. 2, showing the operation on the current data sheet-according to the first embodiment.

Also, if data is inputted by the drawing in the writing (input) mode on the current data sheet 25 shown in FIG. 3, the inputted data is displayed as stroke data, and is quickly reflected also on the current data sheet 25s provided in the size-reduced display area 22. It is noted that the date of first entering the data to the current data sheet 25 is obtained from the system and the date is displayed on the sheet forming date section 26.

If an operation depicted by 301 is performed to determine a desired area in the data processing (control) mode, the surrounded desired area is colored with a translucent color, to explicitly display the selection of the desired area. Thereafter, a recognition button 31 appears on the lower right portion of the actual-size display area 23. Such a recognition button 31 serves to select either image processing or character data conversion.

Herein, consideration is made about converting the stroke data within the selected desired area into character data. In this case, touching a pen on the recognition button, as depicted by 309 enables to convert the stroke data in the selected area into the character data all at once by the use of a character recognition engine provided in the system.

On the other hand, when the image processing is carried out, a line segment is drawn in the data processing (control) mode so as to cross the selected area colored with a translucent color or to be derived in an optional direction. Various kinds of data processings can be selected in accordance with the direction of the drawing.

Now, the recognition button is exemplified as an example of the data conversion means. As mentioned before, it is also possible to perform the data conversion in accordance with the direction of the drawing.

As shown in FIG. 3, the above-mentioned image processing may be executed in the following manners. For example, a movement process is selected when a drawing 302 from the inside of the selected area to the outside is performed while an enlargement process is selected when a drawing 303 from the line (border area) to the outside is performed. Furthermore, a reduction process is selected when a drawing 304 from the line (border area) to the inside of the selected area is performed while a rotation process is selected when a drawing 305 in a desired rotation direction from the line (border area) is performed. Moreover, a deletion process is selected when a drawing 306 from the outside of the selected area to the inside of the selected area, and canceling the selected area is selected when other action is performed. Of course, the image processing is not limited to this, and it is possible to appropriately modify a direction and a starting point thereof. In the illustrated example, when the drawing is stopped at a position, the image in the selected area is fixed at the position.

In addition, processes registered in the pie menu (refer to FIG. 12) are performed in the data processing (control) mode by drawing a line or mark in the eight directions (up and down, right and left, upper and lower right, and upper and lower left) without the area selection.

It is possible to register eight functions in this pie menu, and the registered functions to be performed are determined in accordance with the direction of an operation 307. In the case of a direction a, a process a is selected, in the case of a direction b, a process b (displaying a schema list in this embodiment) is selected, . . . , and in the case of a direction h, a process h is selected. In other words, functions in accordance with the directions in the pie menu can be selected.

As mentioned above, this pie menu is constituted of input supports, such as undo (retry), redo (retry again), and schema (an image of an affected portion) selection and various applications registered in advance. A computing function using handwriting character recognition and a three-dimensional figure forming function are mounted in the latter applications. These applications are displayed as translucent windows placed on the medical record sheet, and an operative application is closed by touching the pen on the outside of the window.

Figure 4:
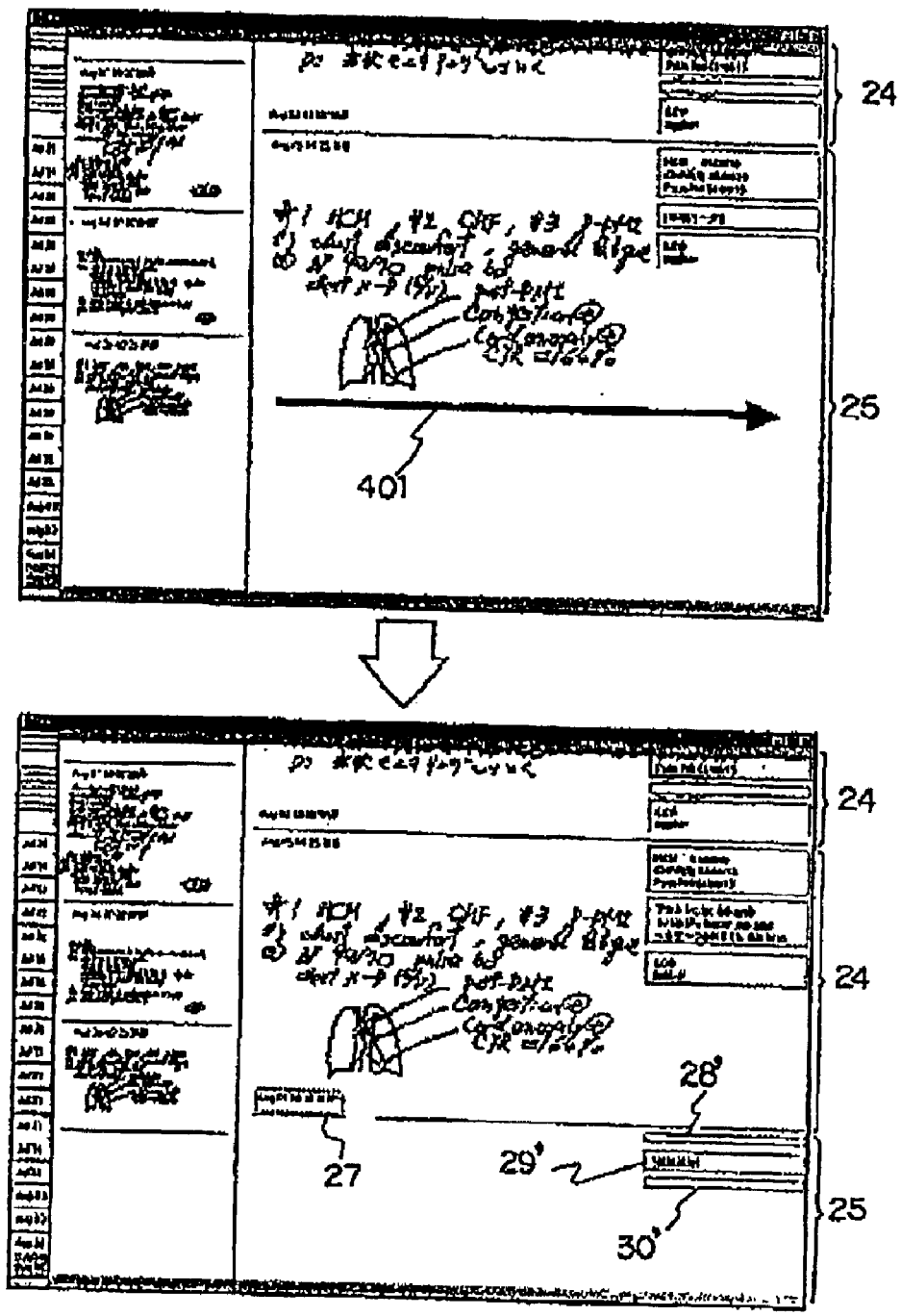
FIG. 4 is an explanatory diagram showing the operation at an end of the medical care according to the first embodiment.

In FIG. 4, an operation 401 of drawing a long straight line on the current data sheet 25 in the writing (input) mode is made so as to clearly indicate the end or finish of the writing of the medical information. After the current time is obtained from the system as an end time of a medical care, the sheet formation finish date section 27 is formed and the obtained time is displayed thereon. Further, the inputted data is blocked or protected so as not to be modified (not to add any data), and the sheet is divided by the partition line (ruled line). Then, the portion on which data input has been finished is displayed as the past data sheet 24, and a portion newly formed is displayed as the current data sheet 25. On the newly formed current data sheet 25, a medical history section 28', a medical prescription request section 29' and a medical check request section 30' are automatically formed. Medical records are stored by the repetition of these operations.

Figure 5:
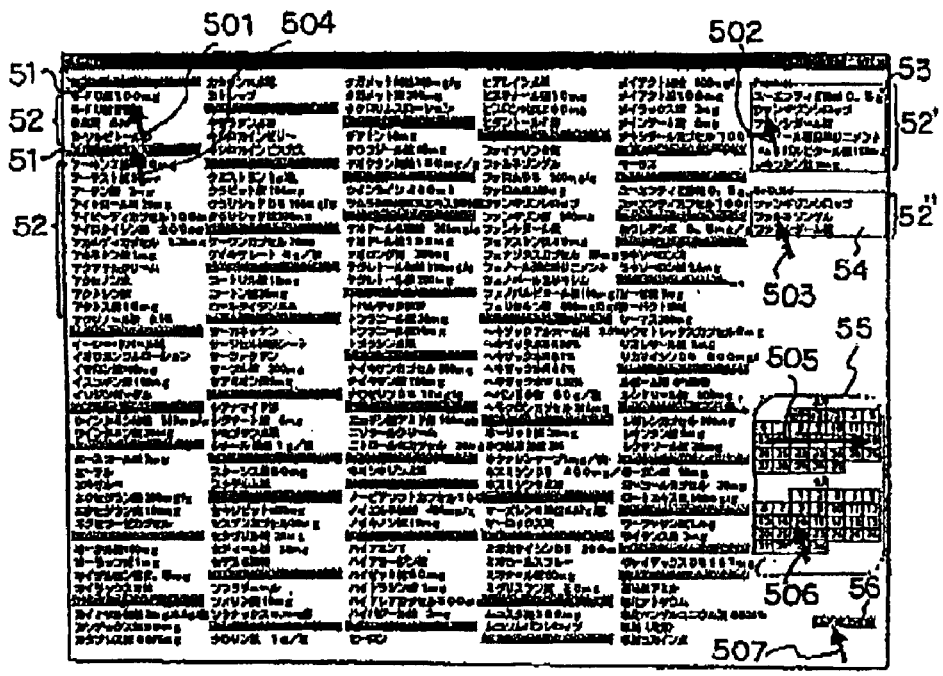
FIG. 5 is an explanatory diagram showing the medicine list selection screen according to the first embodiment.

A medicine list selection screen shown in FIG. 5 is displayed by touching a pen depicted by 308 on a "new order" in the medical prescription request section 29 on the current data sheet 25 in FIG. 3. As shown in FIG. 5, the medicine list selection screen is constituted of an index 51, a medicine name section (names of individual medicines) 52, a previous selected medicine section 53, a selected medicine section 54, a calendar 55, and a finish button 56.

In FIG. 5, the illustrated calendar 55 shows two months (the month including the current day and the next month).

It is impossible to display all of the medicines on the medicine list selection screen because there are so many kinds of medicines.

Therefore, the number of medicine names displayed on an initial screen is controlled so that the percentage of the indexes to the total number may be kept at a predetermined value. The medicine names in the respective indexes displayed on the initial screen are arranged in the order of high frequency of use.

Since there is a high possibility that the medicine inputted in the previous medical care is selected again, the medicine name 52' indicating the medicine inputted in the previous medical care is displayed in the previous selected medicine section 53. This makes it possible to perform a quick input. In addition, when the medicine name 52 Is selected by a pen touch operation 501 and the medicine name 52' is selected by a pen touch operation 502, the selected medicine name is added to the selected medicine section 54 and is displayed in the medical prescription request section 29.

Further, a selected medicine name 52" is deleted in the following manner. Specifically, the medicine name 52" in the selected medicine section 54 is selected by the pen touch operation 502, thereby the selected medicine name 52" is deleted from the selected medicine section 54.

When a medicine name 52 is not displayed on the initial screen, it is selected in the following manner. That is, when the index 51 is selected by a pen touch operation 504, all medicine names 52 linked with the selected index 51 are selectably displayed, and then, a desirable medicine can be selected. By so doing, the selected medicine is registered and displayed on the medical prescription request section 29, the selected medicine section 54, and the medicine name section 52. Thereafter, the display order in the medicine name section 52 is sorted in accordance with the frequency of selection of the medicines, and the number of displayed medicines in the medicine name section 52 is increased/decreased to the number that can be displayed at a time.

A prescription period is determined by the use of the calendar 55 in the following manner. In the case of specifying the period of prescription, the period is selected by a drawing (depicted by 505) in the data processing (control) mode from the corresponding date to the finish date of the prescription. In the case of specifying an optional day, the day is selected by a pen touch operation 506.

When a finish or end button 56 is selected by a pen touch operation 507, the selection of medicines to be prescribed is finished, and the medical record screen as shown in FIG. 3 is displayed again. The medicine name 52" added to the selected medicine section is reflected to the medical prescription request section 29 shown in FIG. 3.

Figure 6:
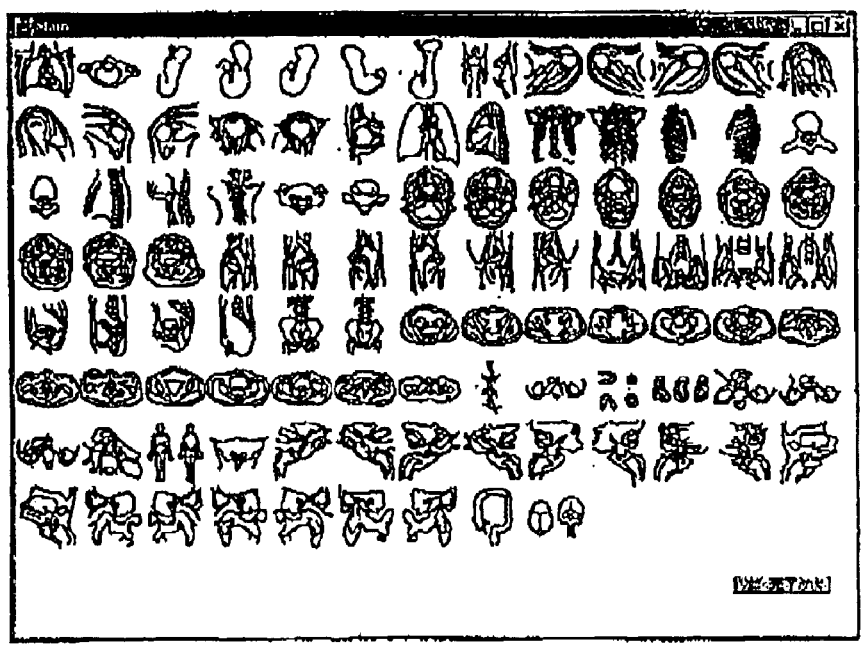
FIG. 6 is an explanatory diagram showing the schema selection screen according to the first embodiment.

A schema list selection screen exemplified in FIG. 6 is displayed by performing a drawing 307b in the data processing (control) mode in the upper right direction (direction b) on the screen shown in FIG. 3. It is to be noted that, as described above, the schema selection is registered in the process b of the pie menu.

By selecting a desired image on the schema selection screen by a pen touch operation, the selected schema is displayed on the medical record screen. Since the selected image is automatically rendered into a selected situation, it is possible to continuously perform such processes as enlargement, reduction, rotation, movement, and three-dimensional operation thereto. The selected image can be moved and pasted on any optional position on the current data sheet 25.

In the illustrated example, though the schema is registered as two-dimensional data, it is also possible to handle the schema as a three-dimensional data by the use of the three-dimensional figure generator.

Also, an image illustrated by a doctor in the writing (input) mode on the actual-size display area can be registered as a schema.

Next, a succession of operations in the electronic medical record system composed as described above according to the first embodiment will be described by the use of FIGS. 7 to 11.

Now, the operation of the entire system will be described in detail with reference to the flow chart in FIG. 7.

First, the system is booted up and a patient number is entered. Then, a desired electronic record of a patient in question is read from the storage device (Step 1). Thereafter, the medical record screen is formed and displayed on the display device (Step 2). In the case of a new patient, a new patient number is inputted. Then, a medical record screen is quickly formed and displayed on the display device (Step 2).

The doctor starts to input medical information (Step 3). In this input operation of the medical information, the process flow is branched in accordance with the mode specified by the pen input. Therefore, it is determined whether the data is inputted in the writing (input) mode or in the data processing (control) mode (Step 4).

In the case of the writing (input) mode (Step 4: Yes), it is determined whether or not the inputted data is a long straight line extending in the transverse direction (Step 5). In other words, it is determined whether the inputted data is representative of a normal stroke or the partition line. An algorithm used in this determination is for judging whether the inputted data is either writing information or partition line information. To this end, the algorithm refers to a relationship between the entire length of the drawing and the straight distance between the starting point and the end point of the drawing, a relationship between the width of the line formed by the drawing and the width of the medical record screen, and a straight distance in the vertical direction of the line formed by the drawing. For example, if the image shown by the drawing satisfies the following three conditions, it is determined that the image shows a partition line.

Condition 1: Total length of the drawn stroke is shorter than 1.2 times the straight distance between the starting point and the end point of the stroke.

Condition 2: The width of the circumscribed rectangle of the drawn stroke is larger than 0.5 time the width of the input screen.

Condition 3: The vertical length of the circumscribed rectangle of the drawn stroke is smaller than 100 pixels.

In the case where the inputted data is not determined to be the partition line (Step 5: No), the inputted data is treated as the stroke data and is subjected to the input process (Step 6), and then the data is displayed on the medical record screen, and the operation flow returns to the input with the pen (Step 3).

In the case where the inputted data is determined to be the partition line (Step 5: Yes), a medical care finish process is performed (Step 7). More specifically, the partition line (ruled line) is displayed on the medical record screen without displaying the image formed by the drawing, and the medical information written until then is stored in the storage device (Step 8) as a polyline (gathered sequence of points) together with positional information and date information. In this manner, the process is finished.

In the case of the data processing (control) mode (Step 4: No), it is determined whether or not any area is selected by the line written by the drawing. An algorithm in this determination is as follows. When the total length of the drawn stroke is longer than twice the straight distance between the starting point and the end point of the stroke, it is determined that the drawn stroke is written to select an area.

When it is determined that the drawn stroke is formed to select an area (Step 9: Yes), an area process is performed to the data in the selected area, more specifically, the surrounded area is colored with a translucent color to show that the area is selected (Step 10). Then, after desired image processings, the system operation returns to the input by a pen (Step 3).

When it is determined that the drawn stroke is not formed to select an area (Step 9: No), a desired pie menu process is performed based on the direction of the drawing (Step 11). After the end or finish of the process, the system operation returns to the input by a pen (Step 3).

Furthermore, the operations in the four processes according to this embodiment will be described with reference to the flow charts in FIGS. 8, 9, 10, and 11.

Figure 7:
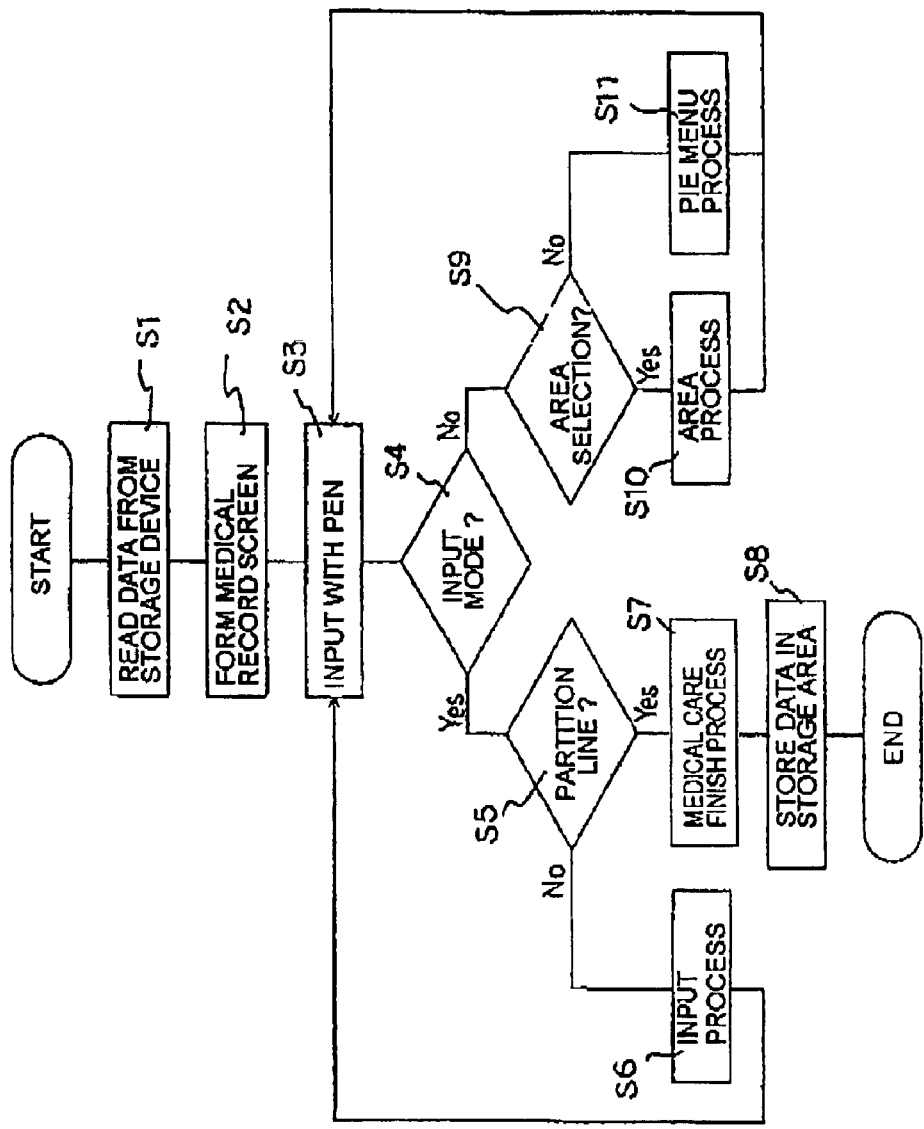
FIG. 7 is a flow chart of the entire system according to the first embodiment.
Figure 8:
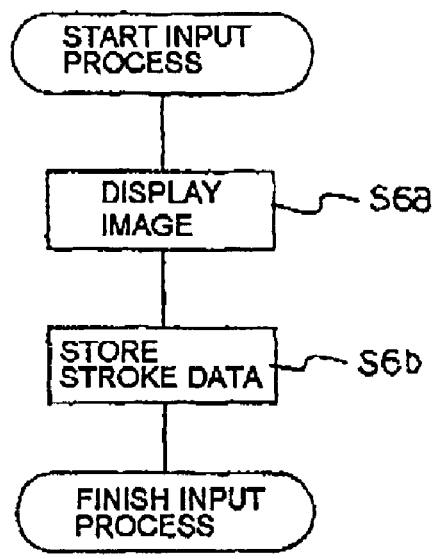
FIG. 8 is a flow chart of the input process according to the first embodiment.

FIG. 8 is a flow chart showing an example of the input process (Step 6) of FIG. 7, in which the inputted image is displayed on the screen (Step 6a), and the stroke data is stored (Step 6b), then, the input process is finished.

Figure 9:
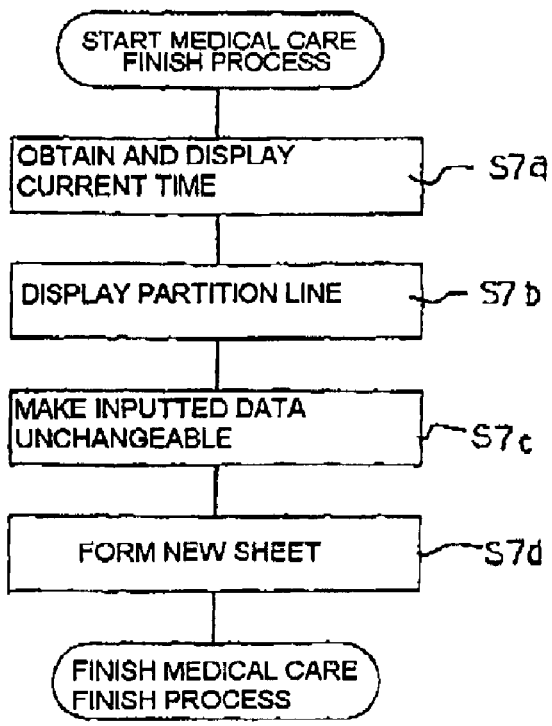
FIG. 9 is a flow chart of the medical care finish process according to the first embodiment.

FIG. 9 is a flow chart showing an example of the medical care finish process (Step 7) of FIG. 7. In this process, the current time is obtained as a medical care finish time (finish of the writing of medical information) from the system and displayed on the screen (Step 7a). Thereafter, the partition line is displayed as a partition of the sheet (Step 7b) and then, the inputted data is made unchangeable (Step 7c). In addition, a new sheet is formed as a preparation for the next medical care (Step 7d), and then, the medical care finish process is ended.

Figure 10:
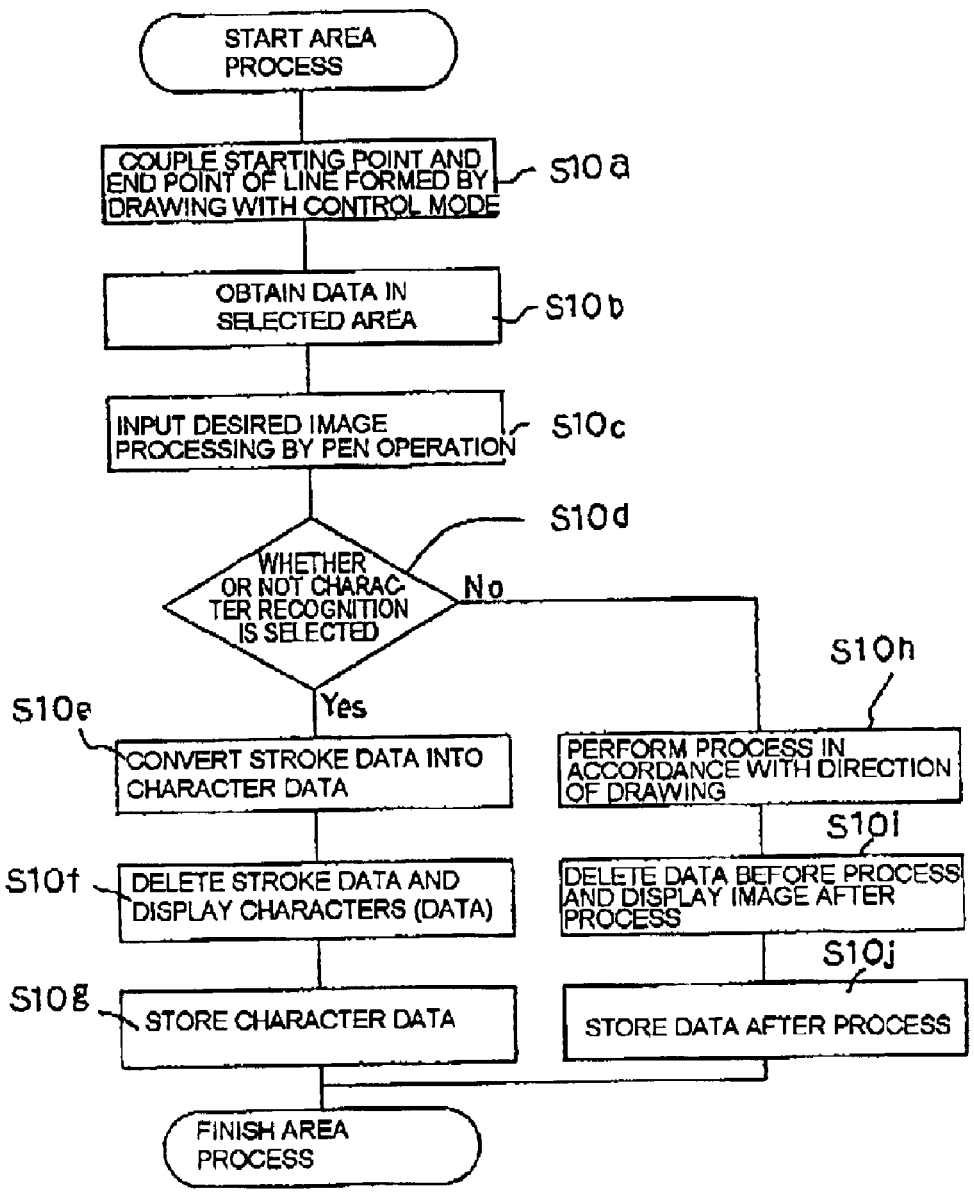
FIG. 10 is a flow chart of the area process according to the first embodiment.

FIG. 10 is a flow chart showing an example of the area process (Step 10) of FIG. 7. In this process, the starting point and the end point of the line shown by the drawing in the data processing (control) mode are coupled (Step 10a), and the surrounded area is colored with a translucent color to clearly show the selected area. Note that it is not always necessary to completely couple the starting point and the end point of the line made by the drawing, and the space therebetween is automatically complemented. When there is no space therebetween, the complement process is of course unnecessary.

Then, the data in the selected area is obtained (Step 10b). By so doing, various processes as described above can be performed to the obtained data, and the desired image processing to be performed is selected by the drawing in the data processing (control) mode (Step 10c).

First, it is determined whether the recognition button is pushed (pen touch) or not (Step 10d). When it is determined that the recognition button is pushed (Step 10d: Yes), the stroke data in the selected area is converted into the character data by the use of the character recognition engine (Step 10e).

Subsequently, the stroke data in the selected area is deleted, and the character data obtained by the conversion is displayed on the screen (Step 10f) and is stored (Step 10g).

When it is determined that the recognition button is not pushed (Step 10d: No), the image processing in accordance with the direction of the drawing in the data processing (control) mode is performed to the data in the selected area (Step 10h).

The image processings include enlargement, reduction, rotation, movement, and deletion as described above. After the image processing, the data before the image processing is deleted, and then, the image after the image processing is displayed (Step 10i) and is stored (Step 10j). In this manner, the area process is finished.

Figure 11:
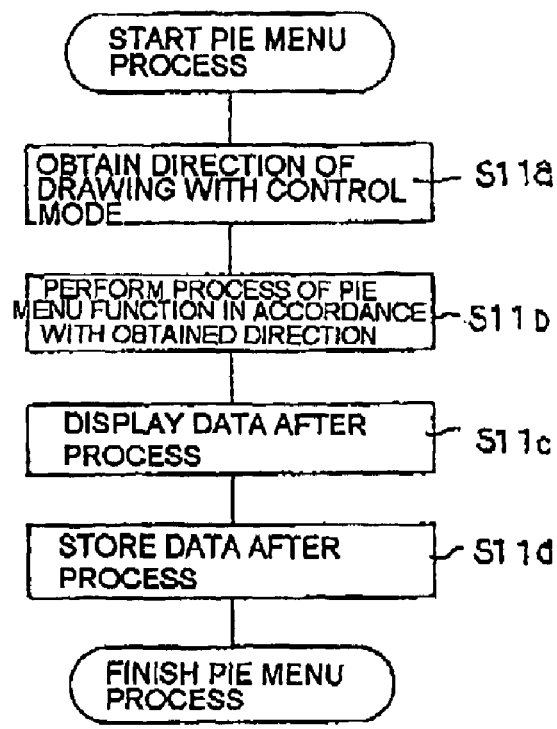
FIG. 11 is a flow chart of the pie menu process according to the first embodiment.
Figure 12:
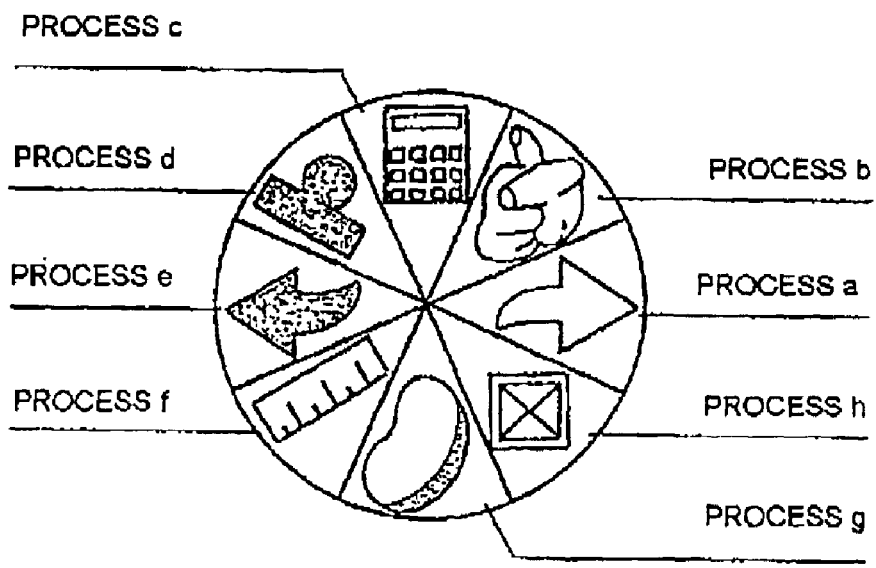
FIG. 12 is an explanatory diagram of the pie menu according to the first embodiment.

FIG. 11 is a flow chart showing an example of the pie menu process (Step 11) of FIG. 7. As described above, various applications can be registered in the pie menu, and the functions of the registered applications can be used with a simple operation. First, the direction of the inputted stroke in the control mode from the starting point to the end point is obtained (Step 11a), and then, the process by the function in the pie menu in accordance with the obtained direction is performed (Step 11b). The data after the process is displayed (Step 11c) and is stored (Step 11d). In this manner, the pie menu process is finished.

Second Embodiment

Next, the second embodiment will be described by the use of FIGS. 13 and 14. In this embodiment, there are a plurality of doctors using the input/output unit device, and each of the operators (doctor) of this system has input means with an ID unique to the operator. More specifically, this embodiment takes the security into account by means of a pen with ID. Note that, in this embodiment, the same components as those used in the first embodiment are denoted with the same reference numeral, and descriptions thereof are omitted.

Figure 13:
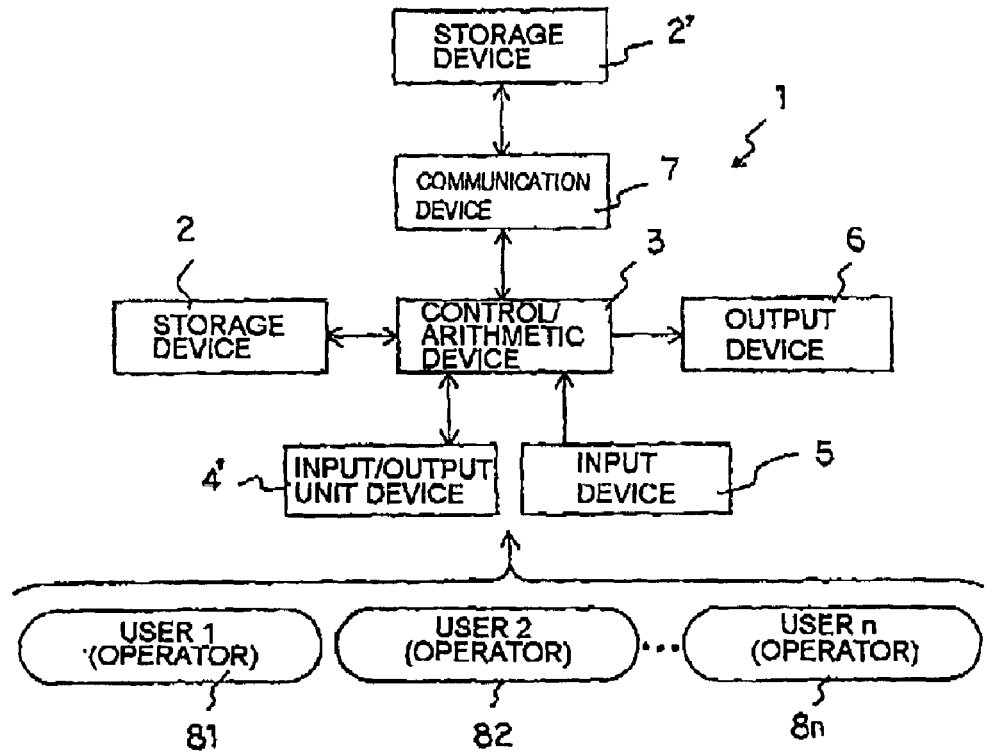
FIG. 13 is a block diagram of the electronic medical record system according to the second embodiment.
Figure 14:
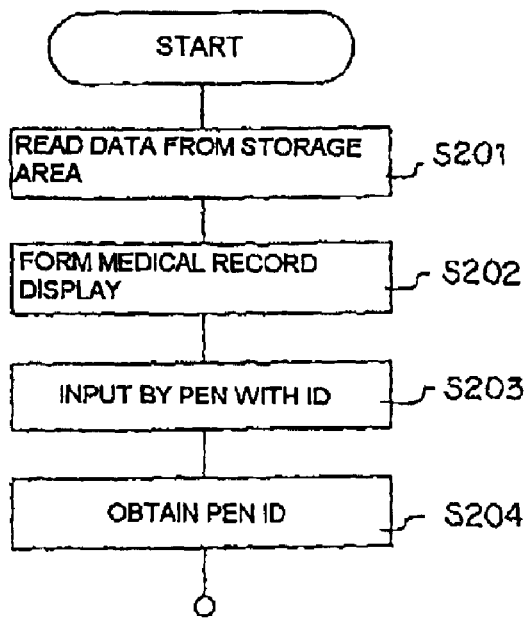
FIG. 14 is a flow chart until the pen ID Is obtained according to the second embodiment.

As shown in FIG. 13, the input/output unit device 4' Is a display device with a tablet function that is a pointing device. The pen for the direct writing on the display screen has an ID function, and the pen is prepared to each of the doctors 81, 82, . . . , 8n that is allowed to operate the system. The IDs added to the pen are different from each other. Note that the system is designed so as not to react to the operation other than that using this allowed pen with an ID.

Next, the operation of the electronic medical record system according to the second embodiment will be described with reference to FIG. 14. Note that the process flow of the second embodiment is equal to that of the first embodiment except that the Steps 1 to 3 (refer to FIG. 7) are replaced with the Steps 201 to 204, and the operations of other steps in the second embodiment are identical to those of the first embodiment. Therefore, the descriptions thereof are omitted.

First, the system is booted and a patient number is inputted. Then, the desired electronic record of a patient is read from the storage device (Step 201), and then, the medical record screen is formed and displayed on the display device (Step 202). In the case of a new patient, a new patient number is inputted. Then, a medical record screen is quickly formed and displayed on the display device (Step 202).

The doctor starts the input with a pen having his/her own ID (Step 203). The system obtains the ID in the inputted data (Step 204) to identify the doctor. The following flow is the same as that from the Step 4 in FIG. 7. However, the second embodiment is different from the first embodiment in that a specific color corresponding to the obtained ID is used to display the data, and the ID data is added when the data is stored. Therefore, it is possible to quickly determine who write the inputted data.

Third Embodiment

Next, the third embodiment will be described by the use of FIGS. 15 and 16. In this embodiment, a data displaying function (sub screen) for displaying time-series information, for example, measurement of body temperature, prescription, and inspection items is added to the first embodiment.

Hereinafter, the displaying of the time-series information on a sub-screen will be described.

Figure 15:
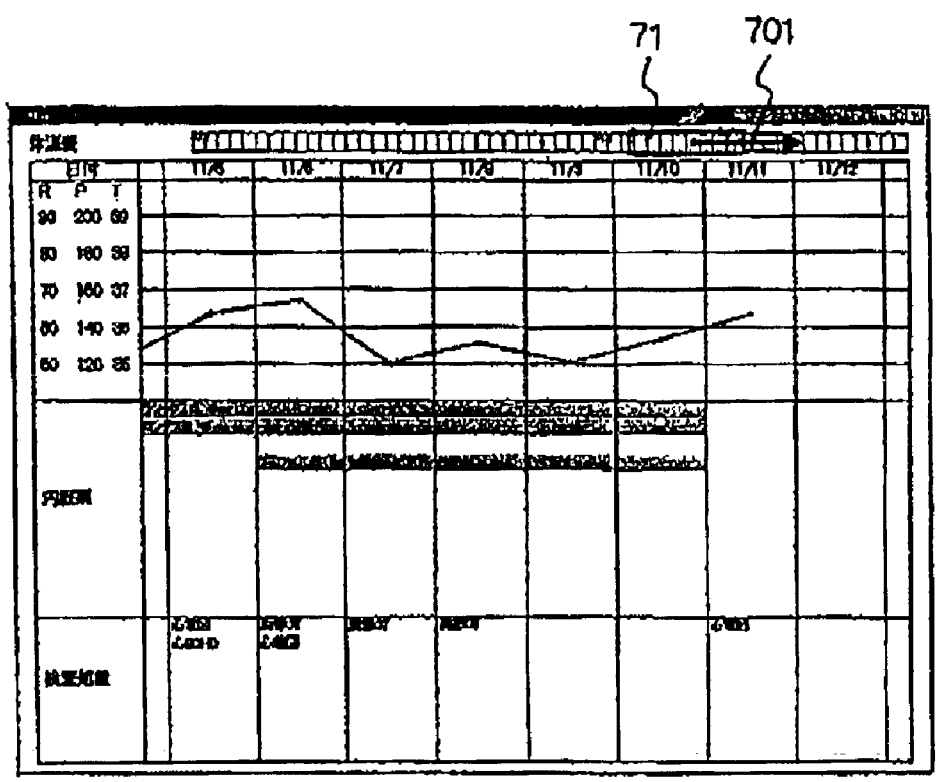
FIG. 15 is an explanatory diagram of a sub-screen of the electronic medical record system according to the third embodiment.

As shown in FIG. 15, the sub-screen is displayed like a long scroll extending in a transverse direction, and the time-series information, for example, measurement of body temperature, prescription, and inspection items is displayed thereon. The sub-screen is scrolled in a drawing direction (horizontal direction) by a drawing 701 with the control mode from the inside of a scroll box.

Figure 16:
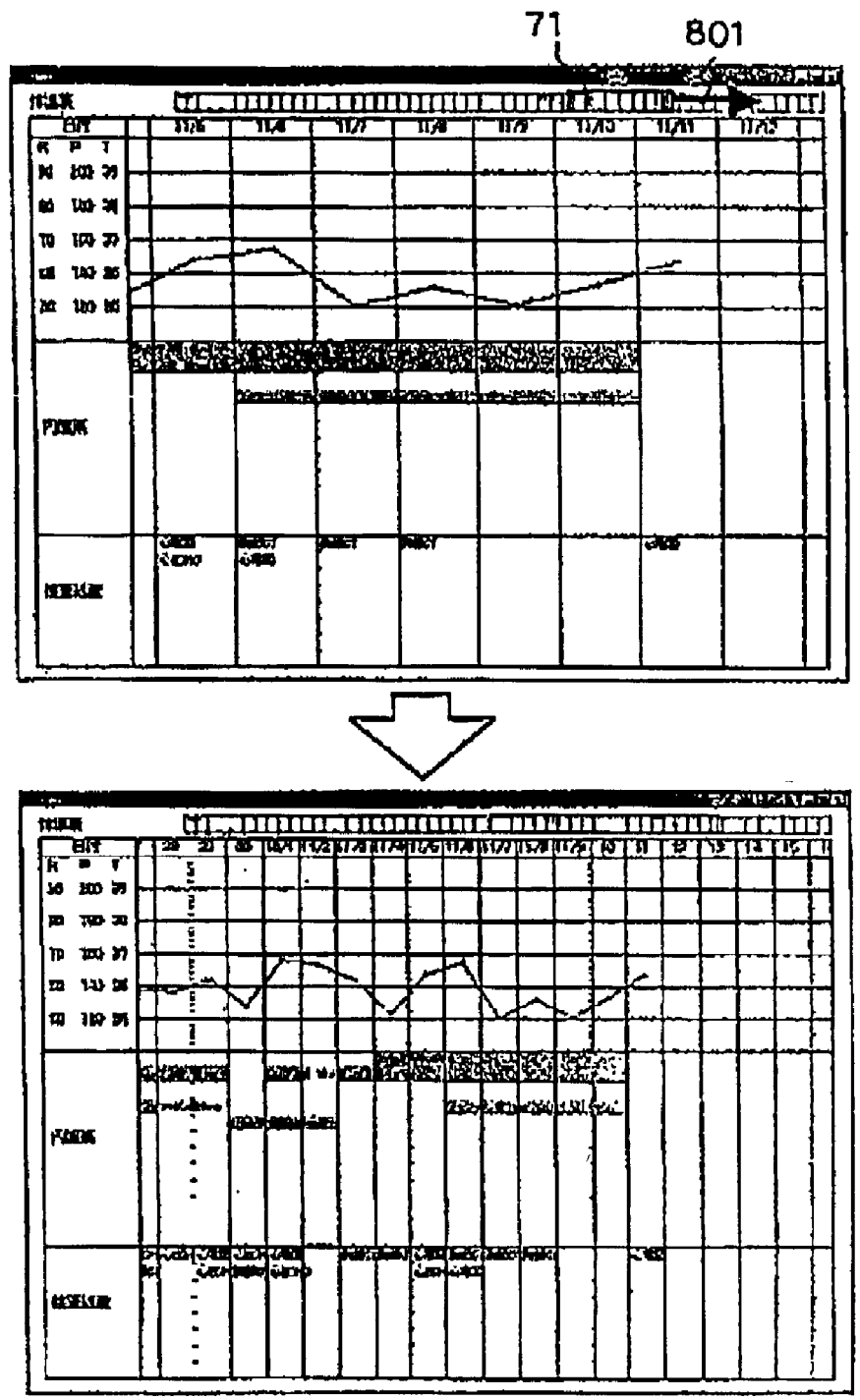
FIG. 16 is an explanatory diagram showing the operation of adjusting the zoom level on the sub-screen.

Also, as shown in FIG. 16, it is possible to adjust the zoom level (display level) by a drawing 801 with the control mode performed after pointing the pen on the edge of the scroll box 71. Therefore, it is possible to overlook the long-term information by reducing the zoom level in the horizontal direction.

In addition, the selection of prescription can be performed on this sub-screen, and it is also possible to specify the period of the prescription by painting the squares of the prescription portion. This operation makes it possible to modify the existing period of prescription and to copy the past prescription. Note that, when a new period is specified, the medicine list selection screen shown in FIG. 5 is displayed so as to select the medicine to be prescribed.

In addition, the sub-screen can be also used to output the medical record screen of a patient having the same symptoms.

In the foregoing, the electronic medical record system according to the embodiments has been described. However, the system is not limited to the embodiments. For example, the settings of the three conditions for determining the partition line (long straight line extending in the horizontal direction) can be appropriately modified. The settings of the three conditions are: the ratio of the total length of the drawn stroke and the straight distance of the stroke (1.2 times in this embodiment); the ratio of the circumscribed rectangle of the drawn stroke to the width of the drawing area (0.5 times in this embodiment); and maximum value of the length of the circumscribed rectangle of the drawn stroke (100 pixels in this embodiment). It is also possible to determine the straight lines in every direction by applying these algorithms.

Similarly, the settings of the conditions for determining the area selection can be appropriately modified. The settings of the area selection is: the ratio of the total length to the straight distance of the stroke (twice in this embodiment).

In addition, the embodiment exemplifies the electronic medical record system. However, the present invention can be realized as a control program for performing the same operations as described above by combining a general-purpose computer and a display device having a tablet function.

The present invention realized by the above-described configurations can achieve the following advantages.

First, since the medical record is displayed as a scroll with an infinite length extending in a longitudinal direction, the input of the medical information is easily performed without taking care of the working area.

Second, since most of the operations for the input are similar to those of writing on the paper by using a pen, the transition from the conventional medical care using the paper writing to the system of the present invention can be easily performed.

Third, since the size-reduced display area and the actual-size display area can be displayed at the same time and can be scrolled independently, the input can be performed while refereeing to the data in the past.

Fourth, since the date display area, the reduced-size display area, and the actual-size display area can be displayed together on a screen and the system has a function to display the past data in succession, it is possible to easily and rapidly search the required data from a great number of medical records.

Fifth, since the past data can be pasted on the current data sheet by only the operations of selecting the past data and drawing a line, it is possible to easily divert the past data.

Sixth, since the arrangement effective to select the medicines to be prescribed is used, it is possible to easily and rapidly select the required medicine from a great number of medicines.

Seventh, since the functions registered in the pie menu can be selected by the simple operation with a pen, it is possible to rapidly select a useful function.

Eighth, since the system can perform the character recognition of the handwritten characters to treat the characters as the character data, the high-speed search with key input can be realized.

Ninth, since many schema images are prepared and the schema image can be used as a three-dimensional schema by the use of the three-dimensional figure forming function, it is possible to easily paste and draw the affected portion of a patient in the findings.

Tenth, since a translucent color is used to show the selected area, it is possible to easily determine the selected area.

While the present invention has thus far been described in a few embodiments thereof, it will be readily possible for those skilled in the art to put the present invention into practice in various other manners. For example, the present invention is applicable to a general electronic record system that has an image screen instead of the medical record screen. In such a general electronic record system, a general electronic record is made up by entering general information and a general image, instead of medical information and a schema, respectively. Moreover, a general request and general items or products are used in lieu of the-prescription request and the medicines, respectively. At any rate, the present invention can provide a user-friendly electronic record system and a control program thereof, in which the free-writing input is realized to reduce the stress due to the complicated input operation.

What is claimed is:

1. An electronic record system comprising:
    an input/output unit device which has a display device with a tablet function and which executes input operation by directly writing input data on a record screen displayed on the display device with a pen; and
    a control/arithmetic device, connected to the input/outout unit device, for processing the handwritten input data onto the display device, so as to formulate an electronic record on the basis of the handwritten input data,
    wherein the record screen of the display device is divided into a reduced-size display area for past information recorded on a past date and an actual size display area for current information recorded by handwriting,
    wherein the control/arithmetic device is configured so that the past information on the reduced-size display area is duplicated onto the actual-size display area by drawing, by the use of the pen, a circular-like shape which surrounds desired past information displayed on the reduced-size display area and by executing drawing from the inside of the handwritten and substantial circle to the outside.

2. The electronic record system according to claim 1, wherein the electronic record is computerized like a stripe-shaped sheet with an infinite length extending in a vertical direction of the record screen, and the control/arithmetic device is configured so that the electronic record displayed on the display device can be scrolled.

3. The electronic record system according to claim 1, wherein the record screen comprises a reduced-size display area on which past information on a past date specified by date information is longitudinally displayed in a reduced size, and an actual-size display area on which detailed information is handwritten and current information is longitudinally displayed in an actual size.

4. The electronic record system according to claim 3, wherein the record screen further includes a date display area for displaying a succession of dates longitudinally.

5. The electronic record system according to claim 4, wherein the control/arithmetic device is configured so that the date display area, the size-reduced display area and the actual-size display area are independently longitudinally scrolled.

6. The electronic record system according to claim 1, wherein the input data comprises written information and data processing information, and the input/output unit device is configured so as to select a writing operation and data processing operation in accordance with an input mode of the pen.

7. The electronic record system according to claim 1, wherein the written information comprises a written record and partition line information that is entered by linear drawing in the horizontal direction of the record screen, so as to end the writing operation, the control/arithmetic device comprising determination means for determining whether the written information is either the written record or the partition line information, and wherein, when it is determined that the written information is the partition line information, a drawn line is not treated as stroke data and a partition line is displayed on the record screen to store the written information.

8. The electronic record system according to claim 7, wherein the determination means determines whether the written information is the written record or the partition line information, with reference to a relationship between an entire length of the drawing and a straight distance from a starting point to an end point of the drawing, a relationship between a width of a line segment formed by the drawing and a width of the record screen, and a straight distance in the vertical direction of the line segment formed by the drawing.

9. The electronic record system according to claim 1, wherein the data processing information comprises area selection information inputted by drawing so as to surround a desired area with a circle and pie menu process information inputted by linear drawing for executing processes registered in advance,
the control/arithmetic device comprising determination means for determining whether the inputted data is the area selection information or the pie menu process information; and wherein, when the determination means determines the inputted data as the area selection information, image processing to the selected desired area is performed, and when the determination means determines the inputted data as the pie menu process information, a data input support process or an application starting process is performed.

10. The electronic record system according to claim 9, wherein the image processing operation includes enlargement, reduction, rotation, movement, duplication, deletion, and character data conversion.

11. The electronic record system according to claim 9, wherein the control/arithmetic device is configured so that image processing operations are selected in accordance with a direction of the drawing performed across the selected area or the drawing performed in an optional direction from the drawn line.

12. The electronic record system according to claim 9, wherein the data input support process is for processing undo, redo and schema,
the control/arithmetic device being configured so that when the schema is selected, a schema image list is displayed and a desired schema image is duplicated on the electronic record by the use of the pen.

13. The electronic record system according to claim 12, wherein the application includes a computing function using handwriting character recognition and a three-dimensional figure forming function for converting the two-dimensional handwritten input or the schema image into a three-dimensional image.

14. The electronic record system according to claim 9, wherein the control/arithmetic device is configured so that the pie menu processes are selected in accordance with a direction of the drawing optionally performed so as not to cross the selected area.

15. The electronic record system according to claim 9, wherein the control/arithmetic device is configured so that when the determination means determines that the inputted data is the area selection information, an area surrounded with a substantial circle is colored with a translucent color to indicate that the area is selected.

16. The electronic record system according to claim 1, wherein the application is adapted to be operated by the use of a translucent window formed on the electronic record, and the application is adapted to be finished by a pen input on the outside of the window.

17. The electronic record system according to claim 1, wherein the control/arithmetic device is configured so that a request section is displayed on the record screen, while a list constituted of index sections and name sections assigned in each index section are displayed by the pen operation on the request section, and a desired name is displayed in the request section by operating the pen on the desired name.

18. The electronic record system according to claim 17, wherein the control/arithmetic device is configured so that an order of items displayed in the name section is sorted in accordance with a frequency of selection of the items, and the list is dynamically modified by increasing/decreasing the number of the names displayed in the name section.

19. The electronic record system according to claim 17, wherein when the pen operation on the index section in the list is performed, all names linked with the index are displayed, and a desired name is displayed on the request section and registered in the name section by the pen operation on the desired name.

20. A computer-readable memory including a program comprising instructions, which when executed cause an electronic record system comprising an input/output unit device which has a display device with a tablet function and which executes input operation by directly writing input data on the display device with a pen;
and a control/arithmetic device, connected to the input/output unit device, for reflecting on the display device the input data entered on the display device to:
display on the display device a record screen in which the input data is intuitively written by direct handwriting; and
establish an electronic record on the basis of the handwritten input information on the record screen displayed by the display step, wherein the electronic record is computerized so as to be a stripe-shaped sheet with an infinite length extending in a vertical direction of the display screen, and the control/arithmetic device is configured so that the electronic record displayed on the display device is scrolled.

21. The computer-readable memory according to claim 20, wherein the record screen comprises a reduced-size display area on which past information in a past date specified by date information is longitudinally displayed in a reduced size, and an actual-size display area on which detailed information is handwritten and current information is longitudinally displayed in an actual size.

22. The computer-readable memory according to claim 21, wherein the record screen further comprises a date display area in which a succession of dates are longitudinally displayed.

23. The computer-readable memory according to claim 22, which is constituted so that the date display area, the size-reduced display area and the actual-size display area are independently longitudinally scrolled.

24. A computer-readable memory including a program comprising instructions, which when executed cause an electronic record system comprising an input/output unit device which has a display device with a tablet function and which executes input operation by directly writing input data on the display device with a pen, and a control/arithmetic device, connected to the input/output unit device, for reflecting on the display device the input data entered on the display device to:
    display on the display device a record screen in which the input data is intuitively written by direct handwriting; and
    establish an electronic record on the basis of the handwritten input information on the record screen displayed by the display step,
    wherein the electronic record is computerized so as to be a stripe-shaved sheet with an infinite length extending in a vertical direction of the display screen, and the control/arithmetic device is configured so that the electronic record displayed on the display device is scrolled,
    wherein the record screen comprises a reduced-size display area on which past information in a past date specified by date information is longitudinally displayed in a reduced size, and an actual-size display area on which detailed information is handwritten and current information is longitudinally displayed in an actual size,
    wherein the record screen further comprises a date display area in which a succession of dates are longitudinally displayed,
    which is constituted so that the date display area, the size-reduced display area and the actual-size display area are independently longitudinally scrolled, and
    wherein the date display area and the reduce-size display area are scrolled together by vertical drawing on these areas, and desired past information is duplicated on the actual-size display area by performing the drawing so as to surround a desired region of the past information displayed on the reduced-size display area with a substantial circle and the drawing from the inside of the circle to the outside.

25. The computer-readable memory according to claim 24, wherein the inputted data comprises written information and data processing information;
    the instructions further comprising causing the electronic record system to select a writing operation and a data processing operation in accordance with an input mode of the pen.

26. The computer-readable memory according to claim 25, wherein the written information comprises a written record and partition line information that is inputted by linear drawing in the horizontal direction of the display screen, so as to finish the writing operation;
    the instructions further causing the electronic record system to:
    determine whether the written information is the written record or the partition line information; and
    treat a drawn line as no stroke data when it is determined that the written information is the partition line information, to display a partition line on the record display screen to store the written information.

27. The computer-readable memory according to claim 26, wherein the determination step determines whether the written information is either the written record or the partition line information, on the basis of a relationship between an entire length of the drawing and the straight distance between a starting point and an end point of the drawing, a relationship between a width of a line segment formed by the drawing and a width of the medical record screen, and a straight distance in the vertical direction of the line segment formed by the drawing.

28. The computer-readable memory according to claim 27, wherein the data processing information comprises area selection information inputted by drawing so as to surround a desired area with a circle, pie menu process information inputted by linear drawing for executing processes registered in advance;
    the instructions further causing the electronic record system to:
    judge whether the inputted data is the area selection information or the pie menu process information;
    carry out image processing to the selected area when the judging step judges the area selection information; and
    carry out a data input support process or an application starting process when the judging step judges the pie menu process information.

29. The computer-readable memory according to claim 28, wherein the image processing includes enlargement, reduction, rotation, movement, duplication, deletion, and character data conversion.

30. The computer-readable memory according to claim 29, which is constituted so that the image processing operations are selected in accordance with a direction of the drawing performed across the selected area or the drawing performed in an optional direction from the drawn line.

31. The computer-readable memory according to claim 30, wherein the data input support process is for processing undo, redo and schema;
    the control program being configured so that when the schema is selected, a schema image list is displayed and a desired schema image can be duplicated on the electronic record by the pen operation.

32. The computer-readable memory according to claim 31, wherein the application includes a computing function using handwriting character recognition and a three-dimensional figure forming function for converting the two-dimensional handwritten input or the schema image into a three-dimensional image, and the respective functions work in cooperation with each other.

33. The computer-readable memory according to claim 32, which is constituted so that the pie menu processes are selected in accordance with a direction of the drawing optionally performed so as not to cross the selected area.

34. The computer-readable memory according to claim 33, which is constituted so that an area surrounded with a substantial circle is colored with a translucent color to indicate that the area is selected, when the judging step judges that the inputted data is the area selection information.

35. The computer-readable memory according to claim 34, wherein the application is adapted to be operated by the use of a translucent window formed on the electronic record, and the application is adapted to be finished by a pen input on the outside of the window.

36. The computer-readable memory according to claim 35, which is constituted so that a request section is displayed on the record screen while a list comprising index sections and name sections assigned in each index section are displayed by the pen operation on the request section, and a desired name is displayed in the request section by the pen operation on the desired name.

37. The computer-readable memory according to claim 36, wherein an order of items displayed in the name section is sorted in accordance with a frequency of selection of the items, and the list is dynamically modified by increasing/decreasing the number of names displayed in the name section.

38. The computer-readable memory according to claim 37, wherein when the pen operation on the index section in the list is performed, all names linked with the index are displayed, and a desired name is displayed on the request section and registered in the name section by the pen operation on the desired name.

39. The electronic record system claimed in claim 1, wherein the electronic record is an electronic medical record.

40. The control program claimed in claim 20, wherein the electronic record is an electronic medical record.

41. The electronic record system according to claim 4, wherein the control/arithmetic device is configured so that the date display area and the reduced-size display area are scrolled together by vertical drawing on these areas.

* * * * *